United States Patent [19]

Korf et al.

[11] Patent Number: 4,805,635
[45] Date of Patent: Feb. 21, 1989

[54] BLOOD COLLECTING VESSEL

[75] Inventors: Dieter Korf, Nuembrecht-winterborn; Eberhard Seibel, Waldbrol-Brol, both of Fed. Rep. of Germany

[73] Assignee: Walter Sarstedt Kunststoff-Spritzgusswerk, Nuembrecht-Rommelsdorf, Fed. Rep. of Germany

[21] Appl. No.: 932,065

[22] Filed: Nov. 18, 1986

[30] Foreign Application Priority Data

Nov. 19, 1985 [DE] Fed. Rep. of Germany ....... 3541041

[51] Int. Cl.4 .............................................. A61B 5/14
[52] U.S. Cl. ..................................... 128/763; 128/767
[58] Field of Search ........................ 128/760, 762–768, 128/770–771

[56] References Cited

U.S. PATENT DOCUMENTS

| 4,024,857 | 5/1977 | Blecher et al. | 128/763 |
| 4,250,893 | 2/1981 | White | 128/767 X |
| 4,397,318 | 8/1983 | Burns | 128/767 X |
| 4,411,163 | 10/1983 | White | 128/767 X |
| 4,576,185 | 3/1986 | Proud et al. | 128/760 |
| 4,608,997 | 9/1986 | Conway | 128/763 |
| 4,646,753 | 3/1987 | Nugent | 128/763 |

Primary Examiner—Kyle L. Howell
Assistant Examiner—Angela D. Sykes
Attorney, Agent, or Firm—Townsend & Townsend

[57] ABSTRACT

A blood collecting vessel has a collecting tube (11) and a blood feed cap (12) with a scoop (16). The scoop (16) subtends an angle of approximately 45° with the normal to the top wall (15) of the blood feed cap (12). (FIG. 1).

26 Claims, 1 Drawing Sheet

BLOOD COLLECTING VESSEL

FIELD OF THE INVENTION

The invention relates to a blood collecting vessel comprising a collecting tube which is closed at the bottom and open at the top, a blood feed cap or blood guiding cap mounted on the open end of the collecting tube, a preferably central inner tube which extends from a preferably central bore in the upper wall of the blood feed cap into the interior of the collecting tube, and a scoop which extends outwardly from the bore in the upper wall, with the front edge of the scoop being engagable with the blood taking surface.

BACKGROUND OF FIELD OF THE INVENTION

In a known blood collecting vessel with a collecting tube an axially directed semi-circular tube is provided in the blood feed cap for the supply of blood, with the flat side of the semi-circular tube being bounded by a wall which is upwardly disposed during the taking of blood and which separates a vent passage from the blood passage. The semi-circular tube extends into the centre of the collecting tube and there directly adjoins the inner wall of the collecting tube (US-PS 43 97 318). Outside of the blood feed cap the semi-circular tube is cut-off obliquely so that a scoop-like projection protrudes in the axial direction by means of which blood can be collecting from a blood collecting surface, for example from an ear lobe or a finger. The disadvantage of this known blood collecting vessel is the fact that it must be held inclined to a greater or lesser degree during the taking of blood, and that the width of the front edge of the scoop-like front part of the semi-circular tube which is placed onto the blood taking surface is restricted by the radius of curvature of the semi-circular tube that is used.

OBJECT OF THE INVENTION

In comparison with this the object underlying the present invention is to provide a blood collecting vessel of the initially named kind in which the taking of blood is also possible without problem when the collecting tube is held substantially vertical, and in which the front edge of the scoop which picks up the blood can have a transverse extent which is not restricted by the radius of curvature of the inner tube.

GENERAL DESCRIPTION

In order to satisfy this object the invention provides that the scoop subtends an angle relative to the central axis of the inner tube, or relative to the normal to the upper wall, or to the central axis of the collecting tube, which is clearly greater than 0° and clearly smaller than 90°.

As a result of the angulation of the invention of the scoop relative to the longitudinal axis of the collecting tube the blood collecting vessel can be moved into position from the side to a blood collecting surface (for example an ear lobe or a finger tip) and can be brought into close contact with the surface. The blood which flows away is first led obliquely via the scoop to the central bore in the blood feed cap from where it is deflected into the vertical direction and can pass with ideal exploitation of its own weight into the collecting tube.

Because, in accordance with the invention, the scoop does not consist of a continuation of the inner tube outwardly, but is instead secured as a practically independent component to the upper side of the blood feed cap, the scoop can be made very broad and flat, in particular in the region of its front edge, in order to reliably capture the blood present in the region of the blood taking surface and to direct it into the bore in the upper wall of the blood feed cap.

A particular advantage lies in the fact that, because the collecting tube can be held vertically during the taking of blood, the level of the blood in the collecting tube, which is preferably provided with a line division, can be precisely observed and if necessary adjusted.

It is particularly advantageous if the angle amounts to from 30° to 60° and in particular to approximately 45°.

In order to reliably guide the blood picked-up by the scoop into the interior of the collecting tube, without the danger of it running past the collecting tube, a further embodiment is so constructed that the scoop extends in the region where it adjoins the bore, over an angle of approximately 180° at the edge of the bore. Furthermore, provision is expediently made for the curvature of the scoop to reduce substantially transverse to its longitudinal extent up to its front edge starting from the bore in such a way that the blade is only curved to a small degree in the region of the front edge. Thus the curvature of the scoop substantially increase in the vicinity of the bore so that the blood which is flowing is gathered together in funnel-like manner and is particularly well-guided. In order to provide both a uniform gradient from the blood flowing over the scoop and to lead the blood without problem to the central bore in the blood feed cap, a further embodiment is characterised in that the side edges of the blade are substantially straight when viewed from the side and extend with increasing curvature in the direciton toward sthe bore starting from the front edge when viewed in plan view.

In order to ensure that the front edge of the scoop can contact a substantially vertical blood taking surface without the surface itself coming into contact with the blood collecting tube, the invention further proposes that the scoop should extend in the radial direction significantly beyond the periphery of the blood feed cap.

The initially mentioned previously known blood collecting vessel consciously renounces the exploitation of capillary forces during the taking of blood. In this way the difficulty associated with the small capillary entry surface in gathering the blood which is to be picked up can be avoided. As a result of this construction it is substantially only the blood which flows as a result of gravity which can pass onto the scoop and enter into the collecting tube. The invention wishes however to connect the advantage of exploiting capillary forces during the gathering of blood with easy blood collection and proposes for this purpose that a capillary groove be provided in the scoop, with the capillary groove leading from the front edge to the inner tube. The capillary groove is in particular arranged at the centre of the scoop. A preferred practical embodiment is characterised in that the capillary groove has a substantially semi-circular cross-section in the region of the front edge. Furthermore, provision should be made that the depth of the capillary groove reduces continuously and preferably linearly in the direction towards the bore starting from the front edge. With this arrangement it is in particular expedient if the depth of the capillary groove reduces to zero at the edge of the bore. The width of the capillary groove should in particular amount to from 1 to 3 and in particular to approximately 2 mm.

As a result of this construction the blood gathered to the side of the capillary tube by the lightly curved gutter-like front edge flows first of all inwardly to the capillary groove where it is principally fed on further to the inner tube by capillary forces. The capillary action is of particular significance in the scoop region because here the slope available for the flowing away of the blood is reduced. As a result of the above described embodiment the invention combines the advantages of a scoop having a very broad front edge with the capillary action which is particularly expedient for the taking of blood.

A further special feature of the invention lies in the fact that the collecting tube has an upper region of larger cross-section, a conically tapering intermediate region and a lower region with a substantially smaller cross-section. The lower region with the smaller cross-section is expediently provided with measuring lines. It is particularly expedient with the above named embodiment when the inner tube extends substantially only within the upper region of the collecting tube, has however a drip projection at one side which preferably extends at least up to the start of the narrowed region, and there expediently has a distance from the wall of the collecting tube which is so small that a blood bridge can form between the drip projection and the inner wall of the collecting tube, either in the narrowing region or below it. The broader upper region of the collecting tube serves primarily to ensure favourable venting during the taking of blood. The blood feed cap is namely placed as tightly as possible on the collecting tube, and is closed apart from a vent hole provided in its upper wall and the opening of the inner tube.

In the above named embodiment it is expedient if the vent hole is located between the inner tube and the peripheral wall of the feed cap in a region where the vent hole at least overlaps the inner space of the collecting tube. The vent hole should thus lie radially as far outwardly as possible in the radial direction in order to preclude as far as possible any contact with the blood located in the collecting tube. In this connection it is also expedient if the vent hole is provided on the side of the upper edge diametrically opposite to the scoop. The vent hole should in particular be directly located at the inner edge of an upper ring flange of the collecting tube. A particularly effective clamped mounting of the blood feed cap can be achieved when the peripheral wall of the blood feed cap has axial ribs at the inside, with the ribs being distributed around the internal periphery of the blood feed cap and clampingly engaging with the upper ring flange of the collecting tube.

In order to keep a closure cap ready at the collecting tube in a simple manner which is particularly expedient during transport and handling a further embodiment is characterised in that a holding ring extends below the ring flange around the upper broadened region of the collecting tube; and in that a tongue formed in one piece with the holding ring leads from the holding ring to a closure cover for the upper region of the collecting tube, with the closure cover being securable on or in said collecting tube after removal of the blood feed cap.

The holding ring is expediently held in such a way that a radially outwardly projecting peripheral rib is provided on the collecting tube closely beneath the holding ring by which the holding ring is latched into its desired position beneath the ring flange.

Furthermore, it is expedient for a mounting of the closure cap which hardly impairs the handling of the blood collecting vessel for the outer diameter of the holding ring to be smaller than the outer diameter of the ring flange by an amount such that the blood feed cap can be placed onto the collecting tube from above with the holding ring in place, with the tongue being bent sharply downwardly and the closure cap being arranged in this way adjacent the lower narrowed region of the collecting tube. In the axial direction the peripheral edge extends downwardly clearly below the holding ring.

The invention will now be described in the following by way of example and with reference to the drawing which shows:

DETAILED DESCRIPTION

Figure 1:
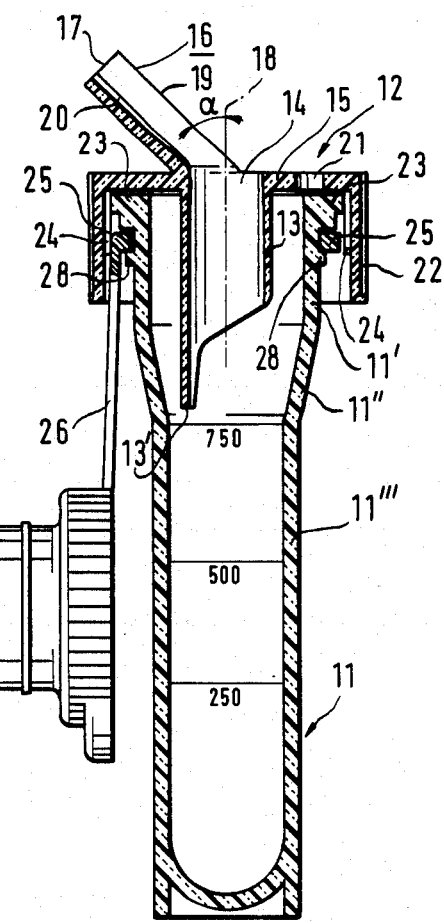
FIG. 1 a partially sectioned schematic sideview of a blood collecting vessel in accordance with the invention, and FIG. 2 a plan view of the subject of FIG. 1.

As seen in the drawing a regular cylindrical collecting tube 11 of plastic having a closed rounded base consists of a lower region 11''' with a relatively small diameter of for example 10 mm, a conically broadening region 11'' which adjoins the top of the lower region and a region 11' of enlarged diameter which is likewise of regular cylindrical shape and is located at the top of the conically broadened region 11'. The upper region 11' is terminated at the top by a radially outwardly projecting ring flange 23, with a peripheral rib 28 being located at a small distance beneath it.

In the lower region 11''' the collecting tube 11 has markings 250, 500 and 750 referring for example to the content, so that the quantity of blood collected in the collecting tube 11 can be estimated or accurately measured.

Figure 2:
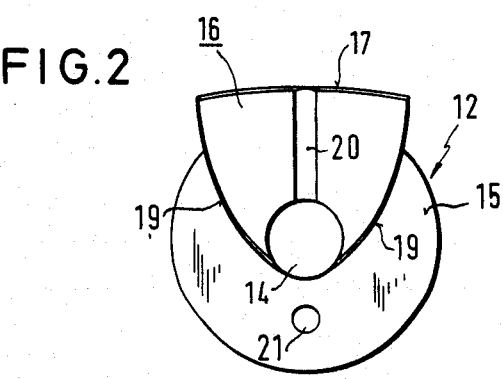

A holding ring 25 of plastic is pushed over the peripheral rib 28 in such a way that the holding ring 25 is retained in its position at the top by the ring flange 23 and at the bottom by the peripheral rib 28. A narrow tongue 26 extends in one piece from a peripheral position on the holding ring 25 to a plastic lid 27 which fits into the upper opening of the collecting tube 11 as a closure lid. As seen in FIGS. 1 and 2 the collecting tube 11 is however initially not closed by the closure lid 27, but instead by a blood feed cap 12 which has an upper wall 15 extending perpendicular to the central longitudinal axis 18 of the collecting tube 11 and radially outwardly a peripheral wall 22 which branches off downwardly from the upper wall 15. The entire blood feed cap 12 with all the parts arranged thereon also consists of plastic.

Radially inwardly, at the peripheral edge 22, axial ribs are molded together with the peripheral edge 22 and are distributed at uniform spacings around the periphery. When the blood feed cap 12 is mounted in accordance with FIG. 1 the ribs 24 clampingly engage with the outer edge of the ring flange 23 so that a reliable retention of the blood feed cap 12 on the collecting tube 11 is ensured.

At the centre the upper wall 15 has a blood feed bore 14 from which an inner tube 13 branches off downwardly, parallel to the central axis 18 and merges at the left hand side of FIG. 1 into a drip projection 13' formed by its correspondingly cut-away wall. The drip projection 13' is rounded at its lower end which terminates close to the upper end of the narrowed region 11''' of the collecting tube 11 and indeed at such a small distance that a blood bridge can be formed there which forwards the blood into the collecting tube 11.

A scoop 16 is provided above the central bore 14 in one piece with the upper wall 15 and projects as seen in the sideview of FIG. 1 at an angle α of approximately 45° to the central axis 18 radially beyond the periphery of the blood feed cap 12. While the scoop is strongly curved in the region of the bore 14, and extends there over an angle of approximately 180° at the edge of the bore 14, it becomes progressively flatter towards its front edge 17 so that a relatively broad front edge 17 is available. The scoop 16 is thus progressively unfolded starting from the region adjacent the bore 14 going in the direction towards the front edge 17, but however still retains a small curvature.

The front edge 17 of the scoop 16 is so constructed that it can be so closely pressed against a blood taking surface, for example the ear lobe or the finger of a person, that blood can flow onto the scoop 16 over the whole front edge 17. The centering of the flow of blood in the direction towards the central bore 14 is favoured by the specially curved side edges 19 of the scoop 16 which can be seen from FIGS. 1 and 2.

At the centre the scoop has a capillary groove 20 which starts from the centre of the front edge 17 and has its deepest position there. In the direction towards the central bore 14, where the capillary groove 20 terminates, its depth reduces linearly to practically zero.

A vent bore 21 is provided on the side of the upper wall 15 diametrically opposite to the scoop 16 near to the ring flange 23.

The peripheral edge of the blood feed cap 12 mounted on the collecting tube 11 presses the tongue 26 downwardly in the manner shown in FIG. 1 so that the closure lip 27 adopts the position shown in FIG. 1 during transport and in use. If desired, the closure ring 17 can be displaced to any desired peripheral position by pivoting the holding ring 25 about the central axis 18.

The manner of operation of the described blood collecting vessel is as follows:

During transport and for the taking of blood the blood vessel adopts the position of FIGS. 1 and 2, i.e. the blood feed cap 12 is set in place and the closure cap 27 at the outside on the collecting tube 11 is pressed downwardly.

The front edge 17 of the upright blood collecting vessel can now for example be applied to a pricked finger cap. The blood flowing out of the wound that is produced flows in this way over the front edge 17 onto the upper surface of the scoop 16 and is led by the latter, in so far as it was not present there at the outset, to the capillary groove 20 which, as a result of capillary action, attracts the blood and conveys it on to the central bore 14 and also into the inner tube 13. A blood bridge then forms between the drip projection 13' and the inner wall of the lower region 11''' of the collecting tube 11 and likewise contributes to the blood rapidly and concentratedly entering into the collecting tube 11 with the cooperation of surface tension forces.

Once the lower region 11''' of the collecting tube 11 is filled in the desired manner with blood the blood feed cap 12 is taken off and thrown away and the collecting tube 11 is hermetically closed by placement of the closure lid 27 mounted thereon. The collecting tube can now be conveyed to a laboratory where for example the collecting tube is inserted into a centrifuge in order to separate the serum from the blood cake.

In accordance with a further embodiment the blood feed cap 12 does not have to be pushed onto the collecting tube 11 as far as is shown in FIG. 1. On the contrary, the clamping ribs 24, which can be alternatively or additionally provided also at the periphery of the ring flange 23, also make it possible for the blood feed cap 12 to be pushed axially onto collecting tube 11 by a substantially smaller amount, for example by only 1 mm. Even better ventilation towards the outside around the ring flange is then ensured.

It is particularly preferred for the ribs 24 to project axially from the top downwardly only by as far as can be recognised in FIG. 1, while the ring flange 23 should however have a somewhat larger diameter corresponding to the internal diameter of the cylindrical peripheral edge 22. In this manner the ribs 24 serve as an axial abutment when mounting the peripheral edge 22 on the ring flange 23. As, in this embodiment, the lower region of the peripheral edge 22 sealingly and clampingly engages outwardly on the ring flange 23, the venting in this case again only takes place via the vent bore 21.

We claim:

1. A blood collecting vessel comprising a collecting tube having a bottom end and a top end, said tube being open at said top end and closed at said bottom end, a blood feed cap mounted on said top end of the collecting tube, said cap having an upper wall, substantially central inner tube which extends from a substantially central bore in said upper wall of the blood feed cap into the interior of the collecting tube, and a scoop which extends outwardly from the bore in said upper wall, said scoop having a front edge, said front edge being engageable with the blood taking surface, characterized in that the scoop (16) subtends an angle (α) relative to the central axis (18) of the inner tube (13), or relative to the normal to the upper wall (15) which is clearly greater than 0° and clearly smaller than 90°.

2. A blood collecting vessel in accordance with claim 1, characterised in that the angle (α) amounts to from 30° to 60° and in particular to approximately 45°.

3. A blood collecting vessel in accordance with claim 1, characterised in that the scoop (16) extends in the region where it adjoins the bore (14) over an angle of approximately 180° at the edge of the bore (14).

4. A blood collecting vessel in accordance with claim 1, charaterised in that the curvature of the scoop (16) transverse to its longitudinal extent reduces significantly starting from the bore (14) and moving outwardly towards its front edge (17) in such a way that the scoop is only curved to a small degree in the region of the front edge (17).

5. A blood collecting vessel in accordance with claim 1, characterized in that said scoop having side edges, said side edges (19) of the scoop (16) are substantially straight when viewed from the side and extend with increasing curvature in the direction towards the bore (14) starting from the front edge (17) when viewed in plan view.

6. A blood collecting vessel in accordance with claim 1, characterised in that the scoop (16) extends in the radial direction substantially beyond the periphery of the blood feed cap (12).

7. A blood collecting vessel in accordance with claim 1, characterised in that a capillary groove (20) is provided in the scoop (16) and leads from the front edge (17) to the inner tube (14).

8. A blood collecting vessel in accordance with claim 7, characterised in that the capillary groove (20) is arranged substantially at the centre of the scoop (16).

9. A blood collecting vessel in accordance with claim 7, characterised in that the capillary groove (20) has a substantially semi-circular cross-section in the region of the front edge (17).

10. A blood collecting vessel in accordance with claim 7, characterised in that the depth of the capillary groove (20) continuously reduces, preferably linearly, in the direction towards the bore (14) satrting from the front edge (17).

11. A blood collecting vessel in accordance with claim 10, characterised in that the depth of the capillary groove (20) reduces to zero up to the edge of the bore (14).

12. A blood collecting vessel in accordance with claim 7, characterised in that the width of the capillary groove (20) amounts to from 1 to 3 and in particular to approximately 2 mm.

13. A blood collecting vessel in accordance with claim 1, characterised in that the collecting tube (11) has an upper region (11') with a larger cross-section, a conically tapering intermediate region (11") and a lower region (11''') with a substantially smaller cross-section.

14. A blood collecting vessel in accordance with claim 13, characterised in that the inner tube (13) extends substantially only within the upper region (11') of the collecting tube (11), has however a drip projection (13') at one side which preferably extends at least up to the start of the lower region (11'''), and there expediently has a distance from the wall of the collecting tube (11) which is so small that a blood bridge can form between the drip projection (13') and the inner wall of the collecting tube (11), either in the lower region (11''') or below it.

15. A blood collecting vessel in accordance with claim 1, characterised in that a vent hole (21) is located in the upper wall (15) of the blood feed cap (12).

16. A blood collecting vessel in accordance with claim 15, characterized in that said feed cap has a peripheral wall and an inner chamber, said vent hole (21) being located between said inner tube (13) and said peripheral wall (22) of said blood feed cap (12) in a region where said vent hole (21) at least overlaps said inner chamber of said collecting tube (11).

17. A blood collecting vessel in accordance with claim 15 or claim 16, characterised in that the vent hole (21) is provided at the side of the upper wall (15) diametrically opposite to the scoop (16).

18. A blood collecting vessel in accordance with claim 15, characterized in that said upper ring flange has an upper edge, said vent hole (21) is directly located at said inner edge of said upper ring flange (23) of said collecting tube (11).

19. A blood collecting vessel in accordance with claim 1, characterized in that said blood feed cap has a peripheral wall and said collecting tube has an upper ring flange, said peripheral wall (22) of the blood feed cap (12) having axial ribs (24) at its inside which are distributed around the periphery and which clampingly ethe blood feed cap (12) having axial ribs (24) at its inside which are distributed around the periphery and which clampingly engage the upper ring flange (23) of the collecting tube (11).

20. A blood collecting vessel in accordance with claim 1, characterised in that a holding ring (25) extends below the ring flange (23) around the upper (broadened) region (11') of the collecting tube (11); and in that a tongue (26) formed in one piece with the holding ring (25) leading from the holding ring to a closure cover (27) for the upper region (11')of the collecting tube (11), said closure cover (27) being securable on said collecting tube after removal of the blood feed cap (12).

21. A blood collecting vessel in accordance with claim 20, characterised in that a radially outwardly projecting peripheral rib or bead (28) is provided on the collecting tube (11) closely beneath the holding ring (25), with the holding ring being latched into its desired position beneath the ring flange (23) over the peripheral rib.

22. A blood collecting vessel in accordance with claim 20, characterised in that the outer diameter of the holding ring (25) is smaller than the outer diameter of the ring flange (23) by an amount such that the blood feed cap (12) can be placed onto the collecting tube (11) from above with the holding ring (25) in place, with the tongue (26) being bent sharply downwardly and the closure cap (27) being arranged in this way adjacent the lower narrowed region (11''') of the collecting tube (11).

23. A blood collecting vessel comprising a collecting tube having a bottom end and a top end, said tube being open at said top end and closed at said bottom end, a blood feed cap mounted on said top end of the collecting tube said cap having an upper wall, a substantially central inner tube which extends from a substantially central bore in said upper wall of the blood feed cap into the interior of the collecting tube, and a scoop which extends outwardly from the bore in said upper wall, said scoop having a front edge, said front edge being engageable with the blood taking surface, characterized in that the scoop (16) subtends an angle ($\alpha$) relative to the central axis (18) of the inner tube (13), or relative to the normal to the upper wall (15), which is clearly greater than 0° and clearly smaller than 90°, said scoop 16 having a capillary groove (20) which leads from the front edge (17) to the inner tube (14).

24. A blood collecting vessel comprising a collecting tube having a bottom end and a top end, said tube being open at said top end and closed at said bottom end, a blood feed cap mounted on said top end of the collecting tube said cap having an upper wall, a substantially central inner tube which extends from a substantially central bore in said upper wall of the blood feed cap into the interior of the collecting tube, and a scoop which extends outwardly from the bore in said upper wall, said scoop having a front edge, said front edge being engageable with the blood taking surface, characterized in that the scoop (16) subtends an angle ($\alpha$) relative to the central axis (18) of the inner tube (13), or relative to the normal to the upper wall (15), which is clearly greater than 0° and clearly smaller than 90°, the curvature of said scoop (16) traverse to its longitudinal extent reducing significantly starting from the bore (14) and moving outwardly towards its front edge (17) in such a way that the scoop is only curved to a small degree in the region of the front edge (17).

25. A blood collecting vessel comprising a collecting tube having a bottom end and a top end, said tube being open at said top end and closed at said bottom end, a blood feed cap mounted on the said top end of the collecting tube said cap having an upper wall, a substantially central inner tube which extends from a substantially central bore in said upper wall of the blood feed cap into the interior of the collecting tube, and a scoop which extends outwardly from the bore in said upper wall, said scoop having a front edge, said from edge being engageable with the blood taking surface, characterized in that the scoop (16) subtends an angle (α) relative to the central axis (18) of the inner tube (13), or relative to the normal to the upper wall (15), which is clearly greater than 0° and clearly smaller than 90°, the collecting tube (11) having an upper region (11') with a larger cross section, a conically tapering intermediate region (11") and a lower region (11''') with a substantially smaller cross section.

26. A blood collecting vessel comprising a collecting tube having a bottom end and a top end, said tube being open at said top end and closed at said bottom end, a blood feed cap mounted on the said top end of the collecting tube said cap having an upper wall, a substantially central inner tube which extends from a substantially central bore in said upper wall of the blood feed cap into the interior of the collecting tube, and a scoop which extends outwardly from the bore in said upper wall, said scoop having a front edge, said from edge being engageable with the blood taking surface, characterized in that the scoop (16) subtends an angle (α) relative to the central axis (18) of the inner tube (13), or relative to the normal to the upper wall (15) which is clearly greater than 0° and clearly smaller than 90°, said scoop being broad and flat in the region of said front edge and relative narrow in the region of said inner tube, the inner tube (13) extending substantially only with the upper region (11') of the collecting tube (11), a drip projection (13') at one side of the inner tube which preferably extends at least up to the start of the narrowed region (11'''), and there has a distance from the wall of the collecting tube (11) which is so small that a blood bridge can form between the drip projection (13') and the inner wall of the collecting tube (11), either in the narrowed region (11''') or below it.

* * * * *